Figure 3:
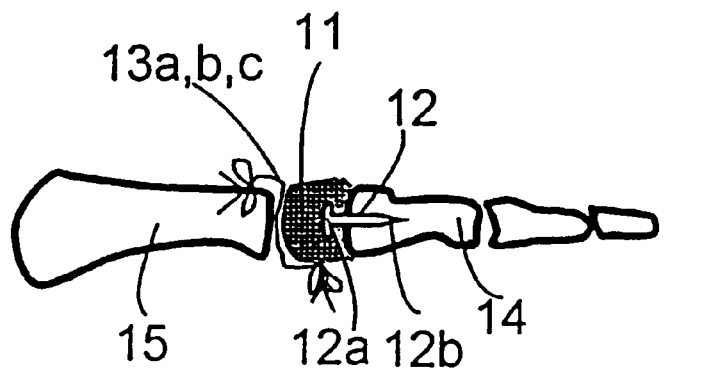
Figure 3:
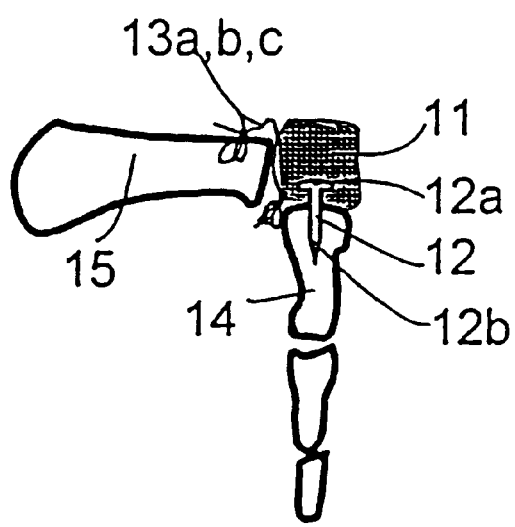
Figure 3:
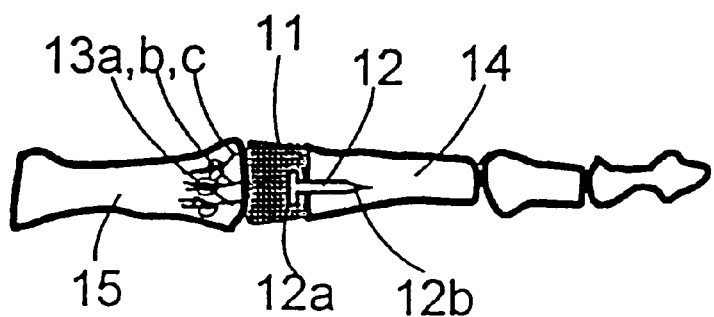

United States Patent
Lehto et al.

[11] Patent Number: 6,007,580
[45] Date of Patent: Dec. 28, 1999

[54] JOINT PROSTHESIS

[75] Inventors: Matti Lehto, Tampere; Mauri Lehtimäki, Kangasala; Senja Paasimaa, Helsinki; Pertti Törmälä, Tampere, all of Finland

[73] Assignee: Bionx Implants Oy, Tampere, Finland

[21] Appl. No.: 08/973,361

[22] PCT Filed: Jun. 13, 1996

[86] PCT No.: PCT/FI96/00351

§ 371 Date: Mar. 11, 1998

§ 102(e) Date: Mar. 11, 1998

[87] PCT Pub. No.: WO96/41596

PCT Pub. Date: Dec. 27, 1996

[30] Foreign Application Priority Data

Jun. 13, 1995 [FI] Finland ................................. 952884

[51] Int. Cl.[6] .................................................. A61F 2/42
[52] U.S. Cl. .................................................. 623/21; 623/18
[58] Field of Search ................................. 623/21, 18, 16

[56] References Cited

U.S. PATENT DOCUMENTS

| | | |
|---|---|---|
| 4,313,232 | 2/1982 | Habal et al. ............................ 623/21 |
| 4,634,445 | 1/1987 | Helal ........................................ 623/21 |
| 4,655,777 | 4/1987 | Dunn et al. ............................. 623/16 |
| 4,873,976 | 10/1989 | Schreiber . |
| 5,201,766 | 4/1993 | Georgette ................................ 623/16 |
| 5,374,268 | 12/1994 | Sander . |
| 5,425,776 | 6/1995 | Cohen ..................................... 623/21 |
| 5,480,447 | 1/1996 | Skiba ....................................... 623/21 |
| 5,507,823 | 4/1996 | Walston et al. ......................... 623/21 |
| 5,534,033 | 7/1996 | Simpson .................................. 623/18 |
| 5,683,466 | 11/1997 | Vitale ....................................... 623/16 |
| 5,702,472 | 12/1997 | Huebner .................................. 623/21 |

*Primary Examiner*—David H. Willse
*Assistant Examiner*—Suzette J. Jackson
*Attorney, Agent, or Firm*—Kenyon & Kenyon

[57] ABSTRACT

The invention relates to a joint prosthesis intended to be mounted between two bones to be joined together. The joint prosthesis comprises a spacer part, intended to be placed between the joint surfaces of the bones to be joined. The spacer part is manufactured of biodegradable polymer, co-polymer, polymer mixture and/or composite. The spacer part is, at least under tissue conditions, porous and elastic. The joint prosthesis further comprises fixation parts which are arranged to fix the spacer part to the bones to be joined, and which are manufactured of biodegradable material.

17 Claims, 8 Drawing Sheets

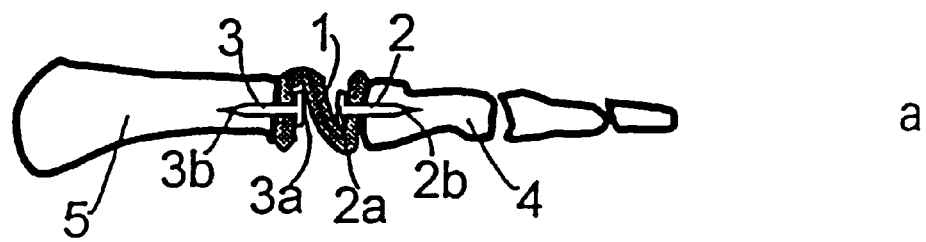
a
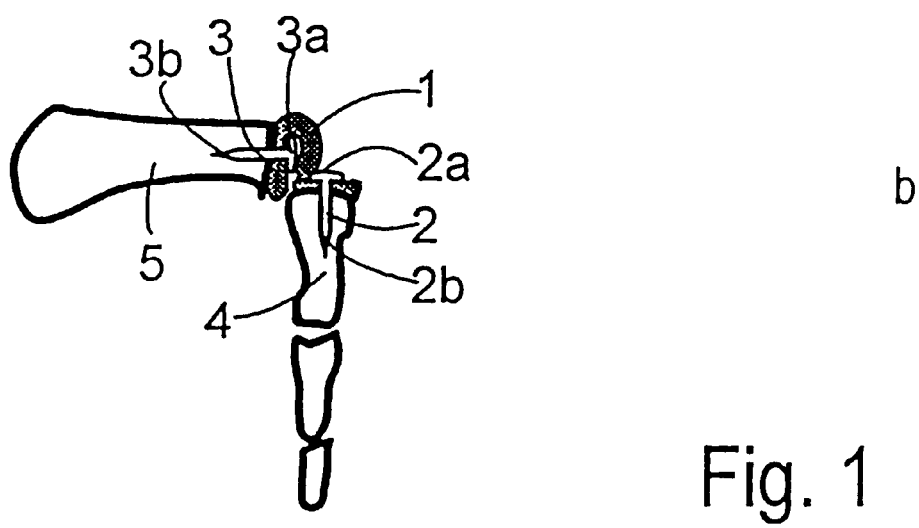
b
Fig. 1
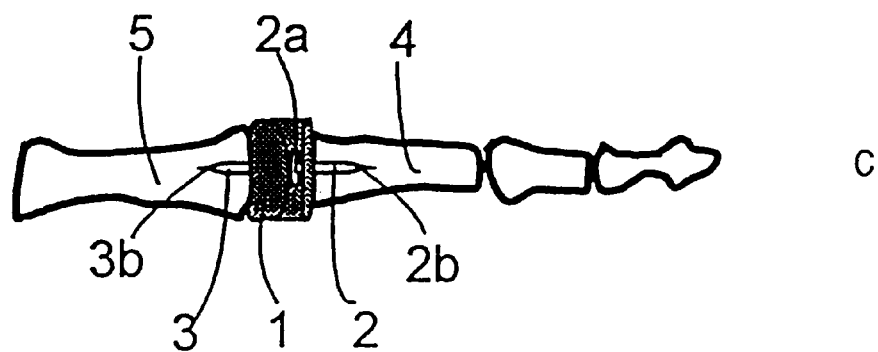
c

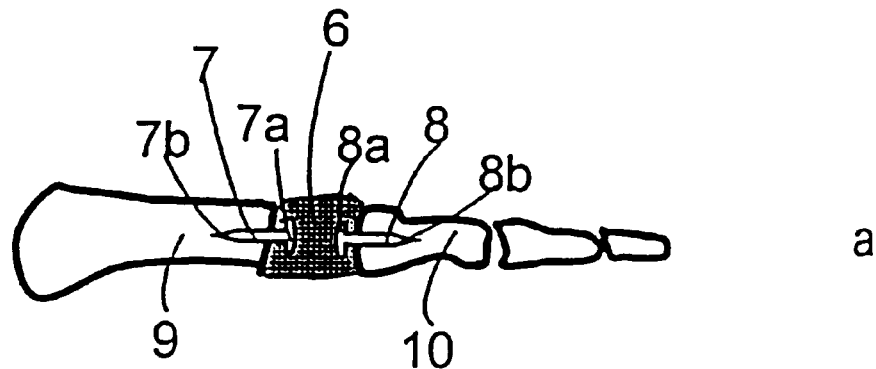
a
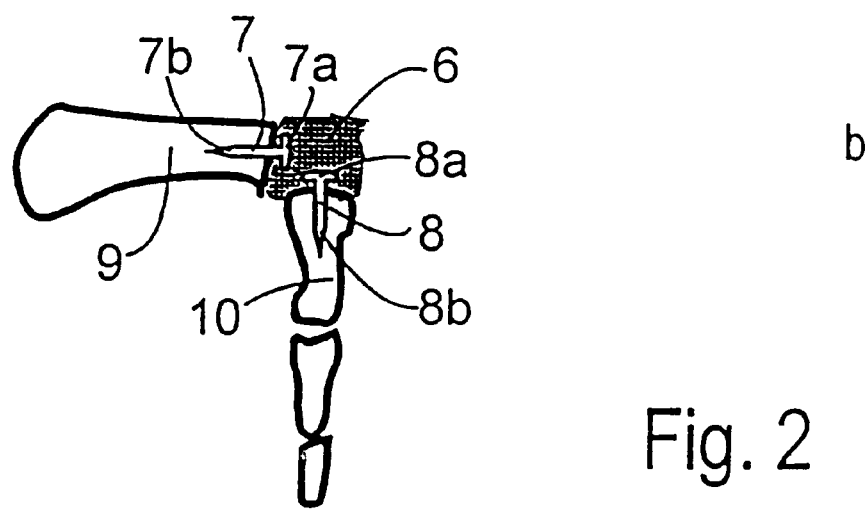
b
Fig. 2
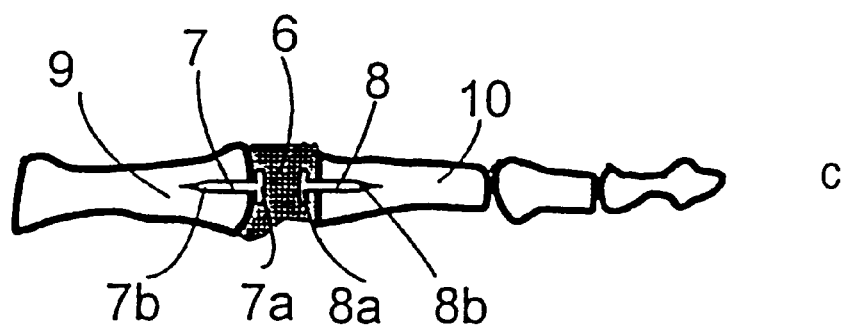
c

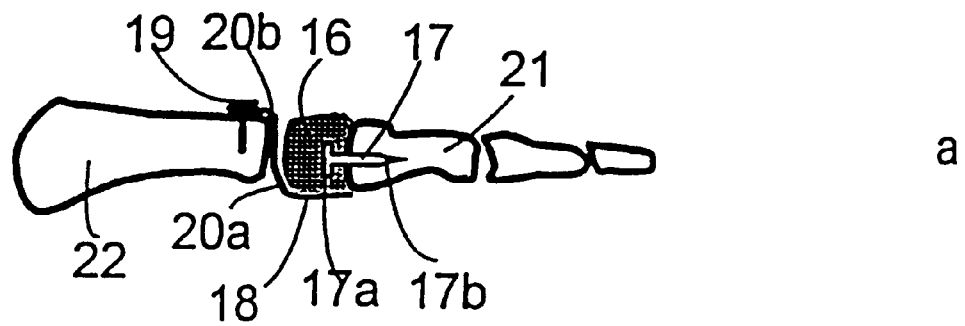
a
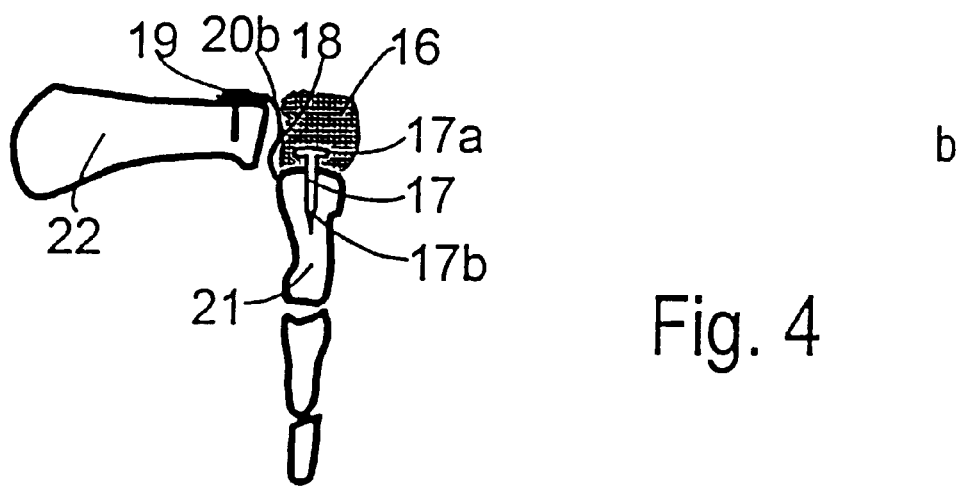
b
Fig. 4
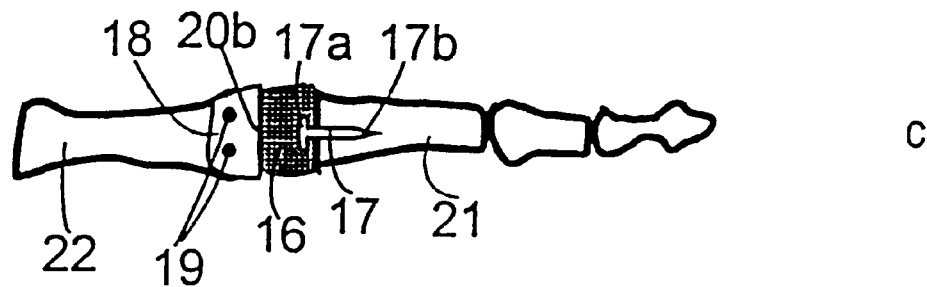
c

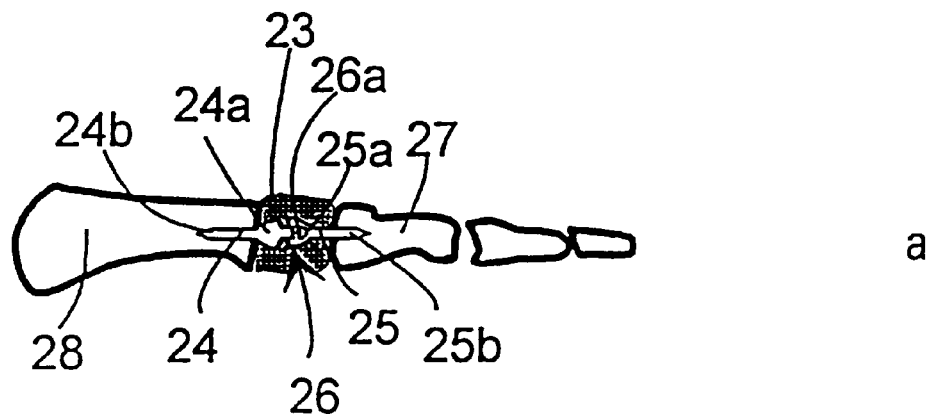
a
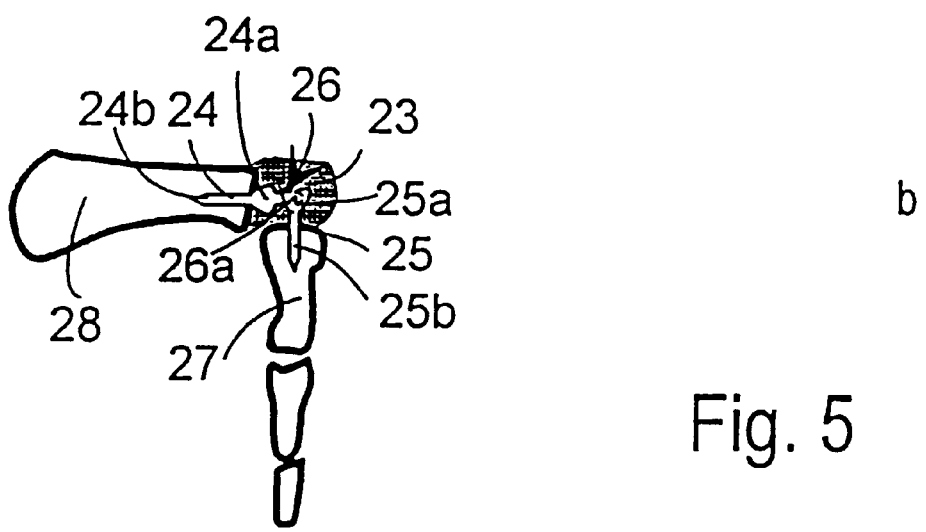
b
Fig. 5
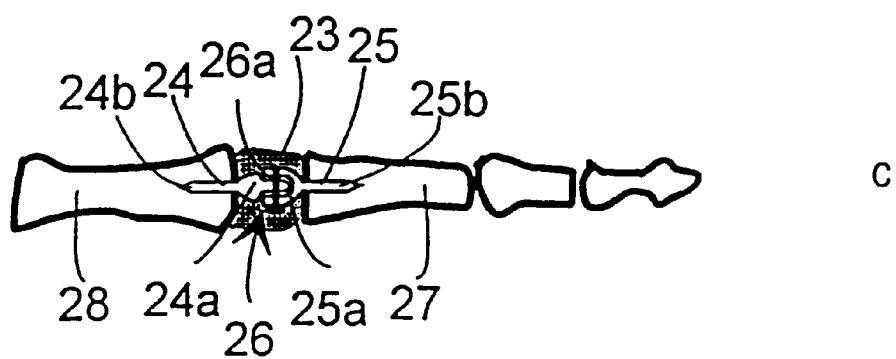
c

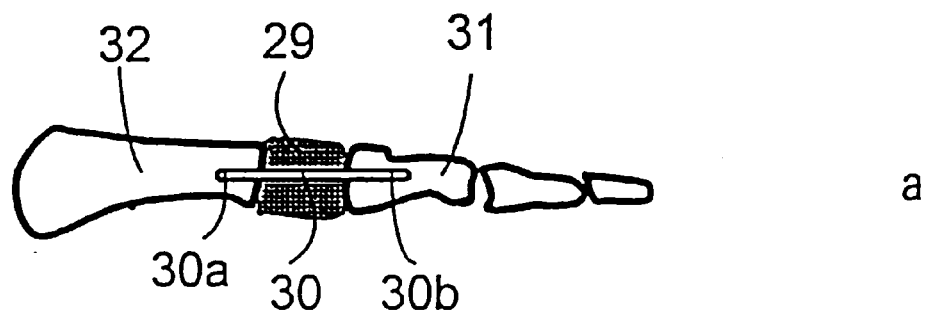
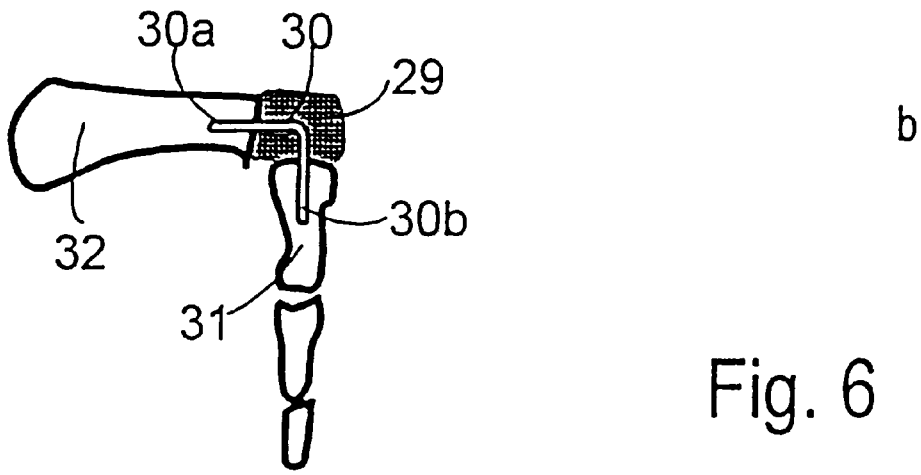
Fig. 6
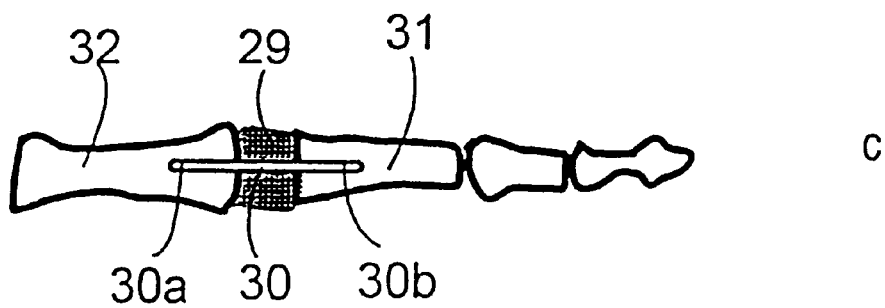

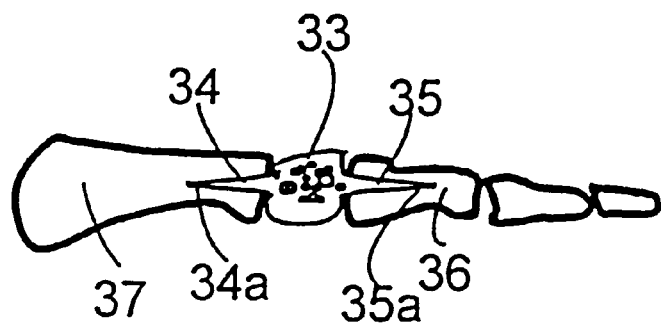
a
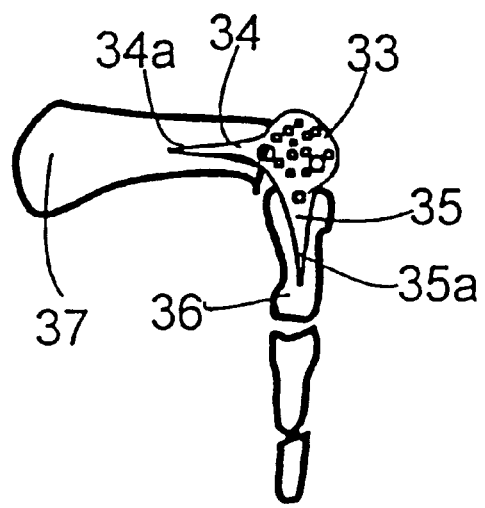
b
Fig. 7
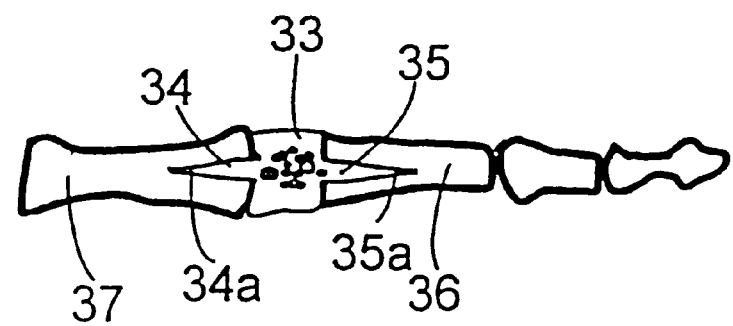
c

JOINT PROSTHESIS

The present invention relates to a joint prosthesis intended to be mounted between two bones to be joined together, wherein the joint prosthesis comprises a spacer part intended to be placed between the joint surfaces of the bones to be joined, and which is manufactured of biodegradable polymer, copolymer, polymer mixture and/or composite, and fixation parts which are arranged to fix the spacer part to the bones to be joined.

In surgery, it is previously known to use synthetic, elastic joint implants made of non-biodegradable plastics to replace joints between small bones in hands and feet. A typical biostable elastic joint prosthesis is composed of (a) a spacer part placed between the bones to be joined, and (b) a proximal and distal elongated fixation part both of which are placed inside the bones to be joined. This type of artificial joint includes for example, Silastic® implants made of silicon elastomer (Manufacturer: Dow Corning S.A., Valbourne Cedex, France).

When inserting an artificial joint, one or both, for example, of rheumatism damaged joint surfaces are customarily removed partially or totally, and inside the joint capsule, an elastic implant is placed to function as joint prosthesis for keeping the bones to be joined at a desired distance from each other, and allowing the joint to be bent by muscular powers. Artificial joint operations in hand, wrist and feet areas are described, for example, in the book "Surgery for Rheumatoid Arthritis," Eds. M. Clayton and C. Smyth, Churchill Livingstone, New York, 1992.

However, the use of joint prostheses manufactured of biostable polymers, polymer mixtures and elastomers may cause problems to the patient. A permanent strain limit for the operated limb has to be set. For example, when Silastic® joint prostheses are used, the operated hand may be strained only with a burden of 5 kg. Overstraining may lead to breaking or wearing of the implant which forms the joint prosthesis.

Furthermore, wearing and/or corrosion may cause that particles come loose of the biostable implant operating as joint prosthesis, which particles effect a chronic inflammation reaction, i.e., a synovitis, and/or osteological changes in the bone. Further, the inflammation reaction may cause tumefaction and pain in the joint even to the degree that the joint prosthesis has to be removed.

It is the surprising discovery of the present invention that by manufacturing an elastic joint prosthesis, mainly according to the manner described in the characterizing part of the claim 1, it is possible to eliminate the above described disadvantages related to prior art solutions and to substantially improve the level of technology applied in the field of surgically inserted joint prostheses, particularly the functionality and strength of the joint provided with a joint prosthesis, and to avoid harmful and chronic foreign substance reactions. It is possible to eliminate the above presented problems typical for biostable joint protheses by means of a joint prosthesis according to the invention, which joint prosthesis is manufactured of biodegradable polymer, co-polymer, polymer mixture or polymer composition in a manner that it is composed of (a) a porous interposition spacer part, and (b) a proximal fixation part fixed in the bones to be joined to each other, and (c) a distal fixation part.

A joint prosthesis in accordance with the invention can be inserted in the hand, wrist or feet areas to replace the damaged joint entirely or partially. The porous spacer part of the prosthesis keeps the bones to be joined at a desired distance from each other. The spacer part is fixed in the bones to be joined by using a proximal and distal fixation part. The strength and ductility values of the fixation parts have been chosen to allow the bending of the operated joint shortly after the insertion operation.

It is characteristic to the joint prosthesis of the present invention that, because the spacer part is porous and biodegradable, a fibrous tissue is induced to form on its surface and inside it. Earlier research has discovered that biodegradable polymer implants induce around and inside themselves formation of fibrous tissue (cf. for example Sasserath, C.; Van Reck, J. Gitani, J., *Acta Stomatologica Belgica* 88, No 1, 1991, pp 5–11; and Ashammakhi, N., Mäkelä, E. A., Vihtonen, K., Rokkanen, P., Kuisma, H. and Törmälä, P., *Biomaterials* 16 (1995), pp. 135–138).

When a porous, biodegradable spacer part containing fibrous tissue continues to biodegrade (typically from 3 weeks to 12 months after the insertion operation, depending on its polymer construction), it is gradually replaced by elastic fibrous tissue which fills the space between the joint intermediate, filled originally by the spacer part, and is fixed in the bones to be joined. Simultaneously or partially after biodegrading of the spacer part, also the proximal and distal fixation part go through a biodegrading process and are replaced by a fibrous tissue and/or bone tissue. As a result, a new, biological, elastic fibrous tissue joint, i.e., "a bioprosthesis," is obtained, which allows moving motion of the joint bones by muscular powers. As the new joint, i.e., the "bioprosthesis," is formed after the degradation process and replacing process of the joint prosthesis entirely of the patient's own tissue, no foreign substance particles harmful to the person's system can come loose, as is the case with a so-called biostable joint prosthesis. Thus, the joint prosthesis in accordance with the invention entirely eliminates the risks to such chronic complications caused by foreign substance particles which are possible when using biostable joint prostheses.

The joint prosthesis according to the invention can be manufactured of biodegradable polymer, co-polymer, polymer mixture or composition, i.e., composition material, or by combining various biodegradable polymer substances. In medical, technical and patent literature, a multitude of biodegradable polymers has been introduced which are suitable for raw materials of joint prostheses in accordance with the present invention. These include, for example, biodegradable alifatic polyesters (cf. for example Vainionpää, S., Rokkanen, P., and Törmälä, P. in *Progr. Polym. Sci.,* 14 (1989), pp. 679–716; patent publications U.S. Pat. No. 4,743,257; U.S. Pat. No. 5,084,051; U.S. Pat. No. 4,968,317; EPO 0423155, patent application PCT/FI93/00014), polyester amids, polyorthoesters, polyanhybrids and polyphosphatsenes (cf. for example C. T. Laurensin et al., *J. Biomed Mater. Res.,* 27 (1993), pp. 963–973).

The porous spacer part of the joint prosthesis in accordance with the invention contains advantageously open porosity, with the pore size varying between 50 μm and 1000 μm. In case the pore size is substantially less than 50 μm, the fibrous tissue cells are not capable of growing inside the porosity. Thus, the spacer part may biodegrade from inside to the degree that it collapses at some stage, wherein the distance between the bones to be joined may become smaller than desired. If the spacer part pores have a larger diameter than 1000 μm, the fibrous tissue can, of course, grow to the pores, but the mechanic strength of the spacer part is not sufficient because of deteriorating strength due to large pore size.

In order to obtain desired porosity (pore size typically between 50 μm and 1000 μm) in the spacer part, it can advantageously be constructed of biodegradable fibers (fiber thicknesses typically between 1 to 300 μm), by manufacturing a fiber forming a three-dimensional, partly porous structure. Manufacturing of structures of this type is known from mechanical textile technology. Biodegradable fibers can be used for weaving cloth or knitting tricot or for manufacturing non-woven cloth and folding or wrapping a three-dimensional, pillow-like, porous spacer part of a construction of this type. It is also possible to use novel, three-dimensional weaving, knitting or twisting techniques of fiber blank in order to manufacture a continuous fiber blank and to cut off suitable pieces for spacer part from such blank. Further, it is possible to bind together biodegradable broken fibers by using biodegradable binding blank to form a three-dimensional spacer structure. It is obvious that also other manufacturing techniques by which porous structures are obtained of broken or continuous fibers are possible when the spacer part is constructed.

The spacer part manufactured of fibers can be made of a single fiber type, such as polyglycolid, polylactid or poly-ε-caprolactone fibers. According to one advantageous embodiment, the spacer part can be manufactured to have a hybrid form by using rapidly degradable fibers and more slowly degradable fibers. A combination of this type is, for example, polyglycolid fibers+poly-L-lactid fibers (for example, in relation 40/60). Thus, the polyglycolid fibers start to degrade rapidly and induce a strong fibrous tissue growth on the surface and inside the spacer part as soon as on the first week after the operation. More slowly absorbing poly-L-lactid fibers maintain the spacer part form for months and do not absorb until over a year later, after the new fibrous tissue joint has been formed and healed to a significant degree.

According to one embodiment, the spacer part can be manufactured of slowly absorbing fibers, which have been coated with a rapidly absorbing polymer. Poly-L-lactid fibers coated with poly-DL-lactid include in combinations of this type. A rapidly dissolving coating induces rapidly the forming of fibrous tissue around and inside the spacer part. More slowly dissolving poly-L-lactid fibers maintain the spacer part form for months and do not dissolve until over a year later, after the new fibrous tissue joint has been formed and healed to a significant degree.

The spacer part can also be manufactured of biodegradable, continuos-constructed polymer blank by producing porosity therein. Porous material of this type can be manufactured, for example, by mixing blowing agent to biodegradable polymer powder or granulate. The blowing agent degrades or evaporates in connection with the melting of the polymer and forms pores (bubbles). Porous biomaterial of this type can be manufactured by extrusion or feeder casting, and spacer pieces of desired size can be cut from the porous blank. Further, by feeder casting it is possible to make spacer pieces of directly the desired size.

Moreover, in plastics technology, a plurality of other methods is known to obtain porosity in a polymer piece. It is possible, for example, during smelting treatment to mix to the biodegradable polymer some additive in powder form, such as some salt, cane sugar, etc., which can be absorbed from the ready-made blank by using a suitable absorbent, such as water, and by using this method to provide open porosity in the blank. An other option is to leave the additive in the spacer part, wherein, under tissue conditions after the surgical operation, it metabolises and in the spacer part develops porosity which is characteristic to it. Furthermore, supercritical carbon dioxide or other gas in over-pressure can be absorbed in the biodegradable polymer blank and blow the blank by using this gas when the pressure is lowered. It is obvious that also other methods for obtaining open porosity to the biodegradable polymer blank are possible when manufacturing the spacer part.

It is advantageous to the spacer part that its form corresponds to the space between the bones to be joined where the spacer part is positioned. Thus, the spacer part can have typically the form of a pillow, cylinder, ellipsoid, (flattened) ball, cubic or rectangular prism, or other three-dimensional structure which as well as possible fills the space constructed for the spacer part between the bones to be joined. The spacer part is advantageously elastic and it may not contain any sharp and/or hard edges or angles which could cause mechanic irritation in the tissue.

The spacer part may have a rigid structure, wherein it does not to any significant extent change its form when the joint is bent. In this situation, the fixation parts have to be flexible and elastic at least for those parts which are situated between the bones and the spacer part, so that the joint can be moved and, in case also the fixation parts are rigid, the spacer part and the fixation parts have to be fixed together by using a flexible joint, for example, a hinge joint.

If the spacer part is flexible, both flexible and rigid fixation parts can be connected thereto.

The spacer part and the proximal and distal fixation parts can be composed of the same biodegradable material (thus, also the fixation parts can possibly contain open porosity, which may fasten the fixation of the fixation parts into the bone due to tissue growth, which is based on porosity) or they may be manufactured as separate parts and connected to one another either before the inserting operation or during the inserting operation to form a flexible and/or elastic entity.

The fixation parts of the joint prosthesis in accordance with the present invention are characterized in that they are joined to the spacer part to form a fixed and integrated entity in a manner that the fixation parts and the spacer part together form a flexible joint prosthesis. By means of the fixation parts, the spacer part is kept between the bones to be joined, wherein by means of muscular power it is possible to bend also the bones to be joined (bending movement of the joints) in relation to each other.

The fixation part can be manufactured of biodegradable polymer, polymer mixture or composition by using a smelting treatment method, such as feeder casting or extrusion, or it can be treated mechanically of a polymer blank or of a piece to a desired form.

Self-reinforced biodegradable compositions are particularly advantageous compositions for raw materials of the fixation parts in accordance with the invention. Compositions of this type have been described in publications U.S. Pat. No. 4,743,257 and WO-88/05312. Also biodegradable compositions of a different type are possible when manufacturing fixation parts according to the invention. Thus, they can be made by reinforcing the biodegradable material by fibers, split fibers, filaments or structures constructed thereof, such as braidings, threads, strings, non-woven structures, cloths, knittings, etc., made of biodegradable polymer, co-polymer or polymer mixture, by combining ready-made fibers with a suitable matrix of polymers. Fibres of this type can be manufactured for example of many polymers mentioned in the reference publications of this invention.

Reinforced fibers of the fixation part can also be biodegradable ceramic fibers, such as biofiberglass or calcium phosphate fibers (cf. for example Vainionpää, S., Rokkanen P., and Törmälä P. in *Prog. Polym. Sci.*, 14 (1989), pp. 679–716).

Fixation parts in accordance with the invention, which are reinforced by biodegradable organic and/or inorganic fibers or structures constructed thereof, can be manufactured by means of different methods in plastics technology by binding the reinforced structures, at least partially, to each other by absorbing polymer, co-polymer or polymer mixture (matrix) under conditions in which, normally when the matrix is in solution or smelt form, a sufficiently homogeneous composition is formed of the matrix and the reinforcing agent. Injection moulding, extrusion, pultrusion, winding, and compression moulding are some possible methods to be used when combining the reinforcing fibers or the like and the matrix, and when forming them into prefabricates and/or instruments.

If desired, also the fixation parts can include open porosity in a similar manner as the spacer part, wherein tissue growth takes place in the open porosity of the fixation part from the surrounding tissue, and as a result of this the fixation part is rapidly locked in its place.

It is obvious that the implants of the invention may also include various additives to facilitate the processability of the material (for example, stabilizers, antioxidants, or softening agents) or to change its properties (for example, softening agents or ceramic chemicals in powder form or biostable fibers, such as carbon fibers) or to facilitate its treating (for example, coloring agents).

The fixation part can also be constructed of the patient's own fibrous tissue, such as cord or ligament tissue, by placing a sufficiently long part of a cord or ligament to extend from one bone to be joined to the other, in a manner that the spacer part is placed between the bones and the cord or ligament penetrates the spacer part.

According to one advantageous embodiment, the spacer part and/or the fixation parts of the invention contain a bioactive agent or agents, such as antibiotics, chemotherapeutic agents, agents accelerating wound healing, agents inducing forming of cartilage collagen, growth hormones, anticoagulant (such as heparin), etc. Bioactive mediums of this type are particularly advantageous in clinical use, because, in addition to the mechanic effect, they have biochemical effects (for example, accelerating the growth of fibrous tissue), medical and other effects in human tissues.

The fixation parts can have a rigid or flexible structure. A rigid fixation part is typically a rod, bar, screw or pin, which is at its stem part connected to the spacer part and whose point is inside the bone to be joined. A profiling (such as a screw thread, various scales or steps) on the surface of a fixation part of this type facilitates the fixation part to lock into the hole made inside the bone. The elastic fixation part can be, for example, a cloth ("a veil") coming out of the spacer part and fixed with small absorbing pins or a suture on the surface of the bone to be joined. The elastic fixation part can also be composed of two or several loops of the absorbing suture which are used for fixing the spacer part to the bone to be joined.

The invention is described in the following description with reference to the examples illustrated in accompanying the drawings, in which FIGS. 1 to 7 illustrate in a schematic longitudinal chart some applications of the joint prosthesis according to the invention to be used for jointing together small bones (such as hand and feet bones), wherein each FIGS. 1 to 7 comprises partial FIGS. *a, b, c* in a manner that the partial FIGS.

*a*) is a schematic chart parallel with the longitudinal axis of the bones, as seen from the side, i.e., from the perpendicular direction against the bending level of the joint, the joint provided with a joint prosthesis being straight,

*b*) is a schematic chart parallel with the longitudinal axis of the bones, as seen from the side, i.e., from the perpendicular direction against the bending level of the joint, the joint provided with a joint prosthesis being bent, and

Figure 8:
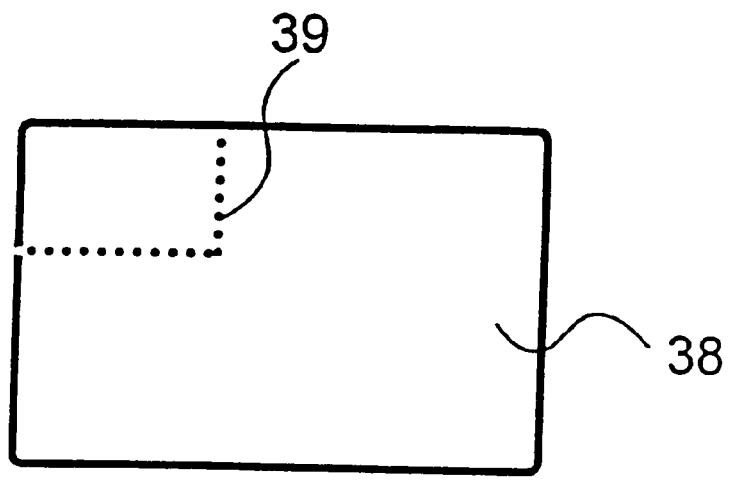
Figure 9:
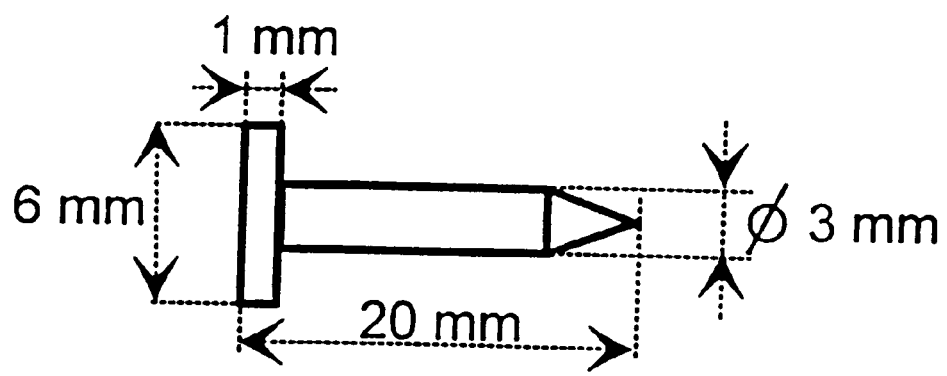

*c*) is a schematic chart parallel with the longitudinal axis of the bones, as seen from above, i.e., from the direction of the bending level of the joint, the joint provided with a joint prosthesis being straight, FIG. 8 illustrates a spacer part application according to Example 1, and FIG. 9 illustrates a fixation part according to Example 3, as seen from the side.

FIGS. 1*a*–*c* to 7*a*–*c* illustrate in outlines the combinations of various rigid and elastic spacer parts and rigid and elastic fixation parts, of which combinations the joint prosthesis according to the invention can be composed of. In order to simplify the schematic charts, the joint capsule connecting the bones to be joined together and surrounding the joint prosthesis is not included.

In FIG. 1 the elastic spacer part is a cloth, string, or braiding 1 constructed of fibers and bent twice, and rigid fixation pins 2 and 3 function as fixation parts penetrating the hems of the spacer part 1, which hems are placed parallel with heads of bones 4 and 5 to be joined. The fixation pins 2 and 3 have stems 2*a*, 3*a* which are on the surface of the hems of the spacer part, and points 2*b*, 3*b* which are inside the bones 4 and 5 to be joined, longitudinally parallel with them.

In FIG. 2 the elastic spacer part is a three-dimensional form part 6 ("pillow") constructed of fibers, and the fixation parts are rigid fixation pins 7, 8 having stems 7*a*, 8*a* which are inside the spacer part, and points 7*b*, 8*b* which are inside bones 9 and 10 to be joined.

In FIG. 3 the elastic spacer part is a three-dimensional form part 11 ("pillow") according to FIG. 2. A first fixation part is a rigid pin 12 having a stem 12*a* which is inside the spacer part, and a point 12*b* which is inside a first bone 14 to be joined. A second fixation part is elastic and composed of three suture loops 13*a*, 13*b* and 13*c*, which are fixed in the spacer part 11 and a second bone 15 to be joined.

In FIG. 4 the elastic spacer part is a three-dimensional form part 16 ("pillow") according to FIGS. 2 and 3. A first fixation part is a rigid pin 17 having a stem 17*a* which is inside the spacer part, and a point 17*b* which is inside a first bone 21 to be joined. A second fixation part is an elastic, elongated cloth 18 ("veil"), substantially of the same width as the spacer part 16, which cloth 18 is connected at its first hem to a spacer part 16, for example, with sutures, and at its second hem to the second bone 22 to be joined, on its upper surface, with small dissolving pins 19, wherein the elastic cloth 18 is fixed, for example, with stitches, on the lower surface of the spacer part 16, and directed with two foldings 20*a* and 20*b* to the second bone 22, in a corresponding manner as with the suture loops 13*a, b, c* of FIG. 3.

In FIG. 5 the elastic spacer part is a three-dimensional form part 23 ("pillow") according to FIGS. 2 to 4. The fixation parts are rigid, elongated fixtures 24, 25, joined together by a hinge joined 26 or the like, and having points 24*b*, 25*b* which are inside bones 27 and 28 to be joined together. The stems 24*a*, 25*b* of the fixtures 24, 25 form hinge joint parts, which are inside the spacer part. The hinge joint has a biodegradable shaft 26*a*, which connects the stem parts 24*a*, 25*a*.

In FIG. 6 the elastic, porous spacer part is a three-dimensional form part 29 in accordance with FIGS. 2 to 5. The form part 29 is penetrated by a fixation part 30, which forms a uniform bar or rod, which is elastic, at least where the spacer part 29 is situated, and having points 30a, 30b which are inside bones 31 and 32 to be joined together.

FIG. 7 illustrates an elastic, porous, blown spacer part 33, and elastic fixation parts 34, 35 formed in connection with and fixed to the spacer part 33, the fixation parts 34, 45 diverging from the spacer part 33 and having points 34a, 35a which are inside bones 36, 37 to be joined.

It is obvious that FIGS. 1 to 7 illustrate only some embodiments of the joint prosthesis according to the invention, in which a porous, elastic spacer part and rigid or elastic fixation parts are connected together to form the joint prosthesis of the invention.

To improve the fixing of fixation parts to a bone, particularly of pin, screw, bolt or rod shaped fixation parts, it is possible to arrange a profiling on their surface.

The functionality of the invention has been described by means of the following non-restrictive examples.

EXAMPLE 1

Manufacturing of the spacer part (pillow) of a commercially available, biodegradable VICRYL hernia pillow:

A spacer part of about 10×15×5 mm was manufactured of a commercially available VICRYL-pillow [(use indication: to support *Transversalis fascia* in inguinal herniaplastics), measurements about 20×50×5 mm, manufacturer: ETHICON, Norderstedt, Germany] in the following manner: a seam 39 was sewn in the hernia pillow 38 with 3-0 bioabsorbing VICRYL thread, as illustrated in FIG. 8 (the pillow is illustrated as seen from above).

Subsequently, the area restricted by the seam 39 was cut off from the original VICRYL-pillow outside the seam, wherein there was obtained a new smaller pillow (measurements about 10×15×5 mm), suitable for the spacer part of the invention.

EXAMPLE 2

Manufacturing of the spacer part of biodegradable co-polymer of L-lactid and ε-caprolactone:

As raw material for the spacer part there was used co-polymer P(ε-CL/L-LA) of ε-caprolactone and L-lactid, the co-polymer having a monomer molar ratio of 25/75 and $M_v \sim 100\,000$ daltons.

Fiber of co-polymer was manufactured by using a single-screw extruder (Axon, Sweden), in which the polymer smelt (T=140 to 170°C.) was extruded through a single-hole (diameter 1 mm) nozzle. After the cooling phase, the obtained monofilament was oriented freely in two phases at a raised temperature. The draw ratio in orientation was 8 to 10. The final fiber diameter was 150 μm.

Tubular knitting was made of the fiber by a cylinder mould machine and a piece of a desired size was cut thereof. The knitting was folded to a multilayer, rectangular prism form in a manner that the shear edges were left inside the foldings. Subsequently, the foldings were fixed together by sewing them fixed at their edges, by using the same fiber the knitting had been made of. In this manner, a uniform spacer part constructed of fibers was obtained, having the measurements 10×16×5 mm.

EXAMPLE b 3

A biodegradable joint prosthesis according to FIG. 3 was manufactured in the following manner:

(A) A fixation part of FIG. 9 was manufactured of P(ε-CL/L-LA) co-polymer 50/50 ($M_v \sim 100\,00$ daltons) by feeder casting, the fixation part having the following measurements: diameter of the stalk of the fixation part 3 mm, total length of the fixation part 20 mm, diameter of the stem 6 mm, and thickness of the stem 1 mm.

(B) A spacer part (measurements 10×15×5 mm) was used, which had been manufactured in accordance with Example 1. A 10 mm long cut, parallel with the long sides of the spacer part was made in the surface knitting in the other side of the spacer part, and the fixation pin in accordance with the paragraph (A) was pressed from the cut inside the spacer part in a manner that the point and stalk of the fixation pin penetrated the spacer part and came out through the other surface of the spacer part. The fixation pin was pressed deep enough inside the spacer part for the broad stem to penetrate inside the spacer part to mix with the broken fiber therein. The cut was closed with 3-0 VICRYL-thread.

The combination of the spacer part and fixation part was closed in a porous sterilization bag and it was sterilized with ethene oxide.

(C) In an operation situation, in the other edge of the spacer part it was fixed by sewing 3 pieces of 3-0 VICRYL-threads to function as a second fixation part in accordance with FIG. 3. These threads were further fixed to the bone to be joined, as illustrated in FIG. 3.

EXAMPLE 4

A spacer part according to Example 2, provided with a pin of Example 3 and a veil of FIG. 4 was manufactured in the following manner:

A two-folded piece of knitted veil was placed partially on top of the folded knitting and subsequently the both knittings were penetrated by a punching knife having the diameter of 3 mm. The pin was pressed through the hole in a manner that its stem remained on the surface of the knitting and its stalk was left outside the knitting. Subsequently, the knitting was folded in a manner that the veil part was at its one end outside the spacer part and at the other end inside the pillow. The edges of the foldings were sewn together by using the same fiber the knitting was made of. The final construction corresponds the FIG. 4.

EXAMPLE 5

A joint prosthesis according to Example 4 used as an artificial joint to replace a knuckle joint.

A transverse skin opening was made at the knuckle joints. The starting point was the MCP II joint, where it was proceeded from an axial opening in the radial side of the extensor joints. At first, synovectom of the joint was implemented. Subsequently, by means of a saw the damaged joint part of metacarpus was resected from the distal size of the collateral ligaments (a piece of about half a centimeter in length corresponding the size of the final prosthesis). After this removal, synovectom was replenished. In case there had been an ulnar deviate position of the fingers, the ulnar collateral ligament and the joint capsule were released if necessary, at the side of the metacarpus, and the radial collateral ligament was tightened. If there, in addition to this, had been a volar subluxation in the joint, the joint capsule was mobilized also on the volar side in a manner that a good dynamic balance was obtained in the joint.

Treating of the bone was started on the proximal phalanx side by making an aperture with a bone drill from the center point of the joint surface to about 2 mm to the volar direction. The aperture was enlarged to correspond the size of the prosthesis by using a core rasp. A fit-joint stalk part which was of the right size was fitted in. Subsequently, the operation area was rinsed with care. The final prosthesis part was carried to its place by pushing the stalk of the pin tightly to the proximal phalanx in a manner that the spacer part which was to remain in the joint was in good contact with the joint surface of the proximal phalanx. Subsequently, in the dorsal side of the distal part of the metacarpus, there was drilled two or three holes having the diameter of 1 mm. The veil like part of the artificial joint was fixed with resorbing pins (Biofix® Mini-tack, manufacturer Biocon Oy, Tampere, Finland) at its place in the bone, after the joint had been reduced from the volar subluxation position to the normal position. Before the pins were fixed, also the ulnar collateral ligament was fixed in order to gain ligament balance of the joint which was more distal than the original one. Finally, centralisation of the extensor joints was implemented at the center of the joint by closing the extended radial retinaculum by duplicating. The resulted situation is shown in FIG. 4.

The patient was allowed to start exercising the operated joint under the control of an occupational therapist as soon as on the second or third day after the operation; a so-called dynamic splint was manufactured to be used in day time and when performing the exercises. The object of the dynamic splint was also to maintain a good position in the fingers during the entire time it was to be used, that is a total of three months, during which time also a so-called rest splint was used during night time. Three months after the operation the patient was taken to the first re-control, wherein motion ranges of the joint, fault position of the fingers and pressing power was measured. Subsequently, the patient was given the permission to discard the splints and gradually to start using the hand in a normal manner. In a re-control, 12 months after the operation, the fibrous joint functioned well, allowing flexion and extension of the knuckle joints and also giving the joints lateral stability together with the reconstructed lateral ligaments.

EXAMPLE 6

The interposition arthoplasty of the MTP I joint by means of joint prosthesis according to Example 2:

A medial skin opening was made over the MTP I joint lengthways over the bunion. The joint capsule was opened lengthways, the proximal phalanx and the metatarsus 1 were prepared subperiostically. The bony prominence connected to the medial side of the MTP 1 was chiselled. Subsequently, a proximal part of about 5 mm was sawed from the proximal phalanx. In the created space, a spacer part according to Example 2 was placed, the fixing of which was made with stitch material to the medial side of the proximal phalanx and metatarsus by means of stitches running through bone canals. Also the medial joint capsule was fixed through bone canals in order to avoid recidivum fault position (valgus).

Supporting splints were manufactured for the patients, which splints were used 2 to 4 weeks by arthrosis patients, and about 6 weeks by rheumatism patients to maintain a good position. During this time, the patients were allowed to walk freely by using a partial shoe which was manufactured in a special manner so that the load is directed on the heel area, and not at all on the operated area. Six weeks after the operation the patients were taken to a re-control and they were given a permission to start taking normal exercises by using shoes with a more solid sole than in normal shoes. Six months after the operation the patients were taken to the final control, wherein an x-ray of the operated foot was taken, in which a fibrous interspace could be seen in the operated joint. In this context, the motion of the joint and the valgus angle of the remedied MTP I-joint were measured.

EXAMPLE 7

Carpo-metacarpo 1 interposition arthoplasty:

A longitudinal cut was made on CMC 1 and the joint capsule was revealed between the joints by taking care of the ramifications of the radial artery and nerve. The joint capsule was opened and it was detached subperiostically from the base of the CMC 1. On both joint surfaces a minimal resection was made in a manner that a proper pumiceous bone surface was shown. Subsequently, bone canals were made between the joint surfaces. The cut was continued in a manner that either extensor carpi radialis longus or palmaris longus joint was shown, from which ⅓ to ½ was taken, in as long a piece as possible, and this piece was transferred freely to the bone canal. The pillow formed spacer part made of PCL-copolymer fiber was used, having a permeable hole at its center. The joint was taken through the hole at the center of the spacer part, and tied dorsally extra-articulately fixed while the spacer part was fitted between the roughed joint surfaces. Subsequently, through the base of the CMC 1 a longitudinal Kirschner spike was taken to carpal bones to the thumb radial abduction. The joint capsule was closed to the transplanted joint in order to obtain as good stability as possible. The Kirschner spike was removed after about four weeks and motion training is started.

It is to be noted that the above mentioned literary sources present a multitude of materials which are suitable for materials in the joint prosthesis in accordance of the invention, in respect of both strength and biodegradable properties. According to these literal and research references, by using the above presented example series as an analog basis, a man skilled in the art can, by applying his or her knowledge in polymers, plastic technology, medicine and surgery, perform the corresponding experiments and testings and prove the functionality of the invention also for other applicable polymers, co-polymers, polymer mixtures and/or compositions known to a man skilled in the art.

We claim:

1. A joint prosthesis intended to be mounted between two bones to be joined together, wherein the joint prosthesis comprises:
    a spacer part intended to be placed between the joint surfaces of the bones to be joined, and which is manufactured of biodegradable polymer, co-polymer, polymer mixture and/or composite, and at least one fixation part arranged to fix the spacer part to the bones to be joined, at least a portion of the fixation part being inside the spacer part, wherein the spacer part and the fixation part are manufactured in separate pieces of one or several biodegradable polymers, co-polymers, polymer mixtures and/or composites and fixed together in order to form a joint prosthesis, and wherein the spacer part is a three-dimensional, uniform form piece which is formed, at least under tissue conditions, to be porous in a manner that the construction comprises continuous and/or broken fibers.

2. A joint prosthesis as set forth in claim 1, wherein the spacer part is a form piece having the form of a pillow, cylinder, ellipsoid, (flattened) ball, cubic or rectangular prism.

3. A joint prosthesis as set forth in claim 1, wherein the spacer part is a string, braiding, cloth, pillow, or non-woven felt.

4. A joint prosthesis as set forth in claim 1, wherein at least one fixation part is composed, at least partially, of at least one thread, braiding or cloth constructed of fiber.

5. A joint prosthesis as set forth in claim 1, wherein at least one fixation part is formed at least partially of one rigid pin, screw, bolt or rod, wherein the stem of the fixation part is situated inside or on the outer surface of the spacer part.

6. A joint prosthesis as set forth in claim 1, wherein fixation parts are joined together inside the spacer part.

7. A joint prosthesis as set forth in claim 1, wherein the fixation part forms at least one uniform, at least partially elastic bar or string which is preferably directed through the spacer part to extend to the bones to be joined.

8. A joint prosthesis as set forth in claim 4, wherein at least one fixation part is constructed of the patient's own fibrous tissue.

9. A joint prosthesis as set forth in claim 1, wherein the porosity of the spacer part is between 50 $\mu$m and 1000 $\mu$m.

10. A joint prosthesis as set forth in claim 1, wherein the spacer part is a composite structure comprising at least two compounds, the structure comprising materials with different degrading times under tissue conditions, wherein the construction of the spacer part is formed by coating a polymer which degrades slower under tissue conditions with a polymer which degrades faster under tissue conditions, and/or by forming the spacer part of polymers having the above mentioned properties in mixture, in fiber form.

11. A joint prosthesis as set forth in claim 1, wherein the spacer part is formed of biodegradable fibers having a typical fiber thickness of 1 to 300 $\mu$m.

12. A joint prosthesis as set forth in claim 2, wherein at least one fixation part is composed, at least partially, of at least one thread, braiding or cloth constructed of fiber.

13. A joint prosthesis as set forth in claim 3, wherein at least one fixation part is composed, at least partially, of at least one thread, braiding or cloth constructed of fiber.

14. A joint prosthesis as set forth in claim 2, wherein at least one fixation part is formed at least partially of one rigid pin, screw, bolt or rod, wherein the stem of the fixation part is situated inside or on the outer surface of the spacer part.

15. A joint prosthesis as set forth in claim 2, wherein fixation parts are joined together inside the spacer part.

16. A joint prosthesis as set forth in claim 6, wherein the fixation part forms at least one uniform, at least partially elastic bar or string which is directed through the spacer part to extend to the bones to be joined.

17. A joint prosthesis as set forth in claim 1, wherein at least one fixation part is constructed of the patient's own fibrous tissue.

* * * * *

UNITED STATES PATENT AND TRADEMARK OFFICE
CERTIFICATE OF CORRECTION

PATENT NO. : 6,007,580
DATED : December 28, 1999
INVENTOR(S) : LEHTO et al.

It is certified that error appears in the above-identified patent and that said Letters Patent is hereby corrected as shown below:

[86] § 371 Date and § 102(e) Date should be - January 16, 1998 -;

Column 2, line 34 "to" should be -- of --;

Column 3, line 37 "include" should be -- are included --;

Column 3, line 45 "continuos" should be -- continuous --;

Column 6, line 59 "joined 26" should be -- joint 26 --;

Column 7, line 62, "EXAMPLE b 3" should be - EXAMPLE 3 -;

Column 8, line 54 "corresponding" should be -- corresponding to --;

Column 8, line 66 "correspond" should be -- correspond to --;

Column 10, line 3 "arthoplasty:" should be -- arthroplasty: --; and

Column 10, line 31 "literal" should be -- literary --.

Signed and Sealed this

Twenty-fourth Day of April, 2001

Attest:

*Attesting Officer*

NICHOLAS P. GODICI

*Acting Director of the United States Patent and Trademark Office*